United States Patent [19]

Urbaschek et al.

[11] Patent Number: 4,861,587

[45] Date of Patent: Aug. 29, 1989

[54] USE OF TNF FOR THE PREVENTION OR TREATMENT OF RADIATION DAMAGE

[75] Inventors: Renate Urbaschek; Berhard Urbaschek, both of Heidelberg; Daniela Maennel, Gaiberg, all of Fed. Rep. of Germany

[73] Assignee: BASF Aktiengesellschaft, Ludwigshafen, Fed. Rep. of Germany

[21] Appl. No.: 37,971

[22] Filed: Apr. 14, 1987

[30] Foreign Application Priority Data

Apr. 18, 1986 [DE] Fed. Rep. of Germany ....... 3613167

[51] Int. Cl.$^4$ .............................................. A61K 37/02
[52] U.S. Cl. ...................................... 424/85.1; 514/2; 514/12; 514/8
[58] Field of Search .......................... 514/2, 12, 8, 917; 530/351; 424/85.1

[56] References Cited

U.S. PATENT DOCUMENTS 4,275,056 6/1981 Takaku et al. ........................ 424/99

OTHER PUBLICATIONS

Muir's Textbook of Pathology, 10th Ed. (1976) pp. 23–29, "Cell Damage Due to Ionising Radiation" and p. 259.
Broudy et al., cited in Chem. Abstracts, vol. 105:189177p (1986).
Carswell et al., PNAS USA, vol. 72, No. 9, pp. 3666–3670, Sep. 1975.
Stankovic, cited in Chem. Abstracts, vol. 74:38912q (1971).
Nature, vol. 312, (1984), pp. 724–729.
Broudy et al. (1986), Proc. Natl. Acad. Aci. USA, 83:7467–7471.
Activation of Human Polymorphonuclear Neutrophil Functions by Interferon-$\gamma$ and Tumor Necrosis Factors, J. of Immuno. (1985)135, No. 3:2069–2073—Shalaby et al.

Primary Examiner—Johnnie R. Brown
Assistant Examiner—Jacqueline M. Stone
Attorney, Agent, or Firm—Keil & Weinkauf

[57] ABSTRACT

The use of TNF for the prophylaxis and therapy of radiaton damage is described.

1 Claim, No Drawings

USE OF TNF FOR THE PREVENTION OR TREATMENT OF RADIATION DAMAGE

TNF (tumor necrosis factor) is a tumor-destroying substance which is intended to be used for the treatment of malignant tumors. The structure of this substance has been described in Nature 312 (1984), 724.

We have found that TNF is also useful for the prophylaxis and therapy of radiation damage.

The present invention relates to the use of TNF for the preparation of drugs for the prophylaxis and therapy of radiation damage and to the use of TNF for the prophylaxis and therapy of radiation damage.

Radiation damage manifests itself, for example, in bone marrow suppression, infectious diseases, gastrointestinal disc orders and/or damage to the central nervous system.

Since TNF is a polypeptide which is destroyed in the gastrointestinal tract, it can only be administered parenterally, preferably intravenously. Sterile isotonic solutions are suitable for this purpose. These can be prepared, for example, by dissolving the TNF in a blood-isotonic aqueous solution, subjecting the solution to sterile filtration and introducing it into ampoules. The pH of the solution is preferably from 5 to 8, in particular about 7.5.

The dose to be administered is from 0.1 to 5, preferably from 0.5 to 3, mg of TNF per patient per day. The duration of treatment is as a rule from 1 to 6 days.

The efficacy of the TNF has been demonstrated, for example, as follows:

40 C3H/HEJ mice were exposed once to X-radiation at a level of 660 rad. 20 mice had been injected intravenously with 5 μg of TNF 24 hours before exposure to radiation, and 20 mice were injected intravenously with the same dose of TNF 24 hours after exposure to radiation. The mice were observed over a period of 30 days after exposure, in order to determine the mortality rate. During this period, 40% of the animals died. In a control group which had not been treated with TNF, 75% of the animals died under the same conditions.

Preparation of an administration form 100 mg of TNF are dissolved in 300 ml of 20 mM sodium phosphate buffer at pH 7.5. The solution is made blood-isotonic with sodium chloride and subjected to sterile filtration over a pore filter (pore size 0.1 to 0.2 μm), and 5 ml portions are introduced into ampoules by a sterile procedure.

We claim:

1. The method of preventing or treating radiation damage in a patient, which comprises administering an effective amount of TNF.

* * * * *